United States Patent [19]

Weder

[11] Patent Number: 5,242,052
[45] Date of Patent: * Sep. 7, 1993

[54] ANTIMICROBIAL MATERIAL AND METHODS

[75] Inventor: Donald E. Weder, Highland, Ill.

[73] Assignee: Highland Supply Corporation, Ill.

[ * ] Notice: The portion of the term of this patent subsequent to Feb. 5, 2008 has been disclaimed.

[21] Appl. No.: 826,579

[22] Filed: Jan. 27, 1992

Related U.S. Application Data

[62] Division of Ser. No. 538,293, Jun. 14, 1990, abandoned.

[51] Int. Cl.⁵ .................................................. D21H 21/36
[52] U.S. Cl. ...................................... 206/423; 424/409; 424/411; 424/412; 424/414; 424/415; 428/19; 428/22; 428/23; 428/906; 428/907; 47/72
[58] Field of Search ............. 424/414, 415, 409, 411, 424/412; 428/906, 907, 19, 22, 23; 47/72; 206/423

[56] References Cited

U.S. PATENT DOCUMENTS

| | | | |
|---|---|---|---|
| 107,690 | 9/1870 | Jaques | 424/415 |
| 1,048,674 | 12/1912 | Fitzgerald | 424/415 |
| 1,447,615 | 3/1923 | Dallam | 424/415 |
| 2,047,975 | 7/1936 | Liberthson | 424/415 |
| 2,051,170 | 8/1936 | Helfrich | 428/486 |
| 2,707,352 | 5/1955 | Fischer | 47/58 |
| 2,813,056 | 11/1957 | Davis et al. | 424/618 |
| 2,833,669 | 5/1958 | Ziegler | 427/308 |
| 2,906,646 | 9/1959 | Smith et al. | 424/415 |
| 3,044,885 | 7/1962 | Loehr | 424/413 |
| 3,069,252 | 12/1962 | Josephs et al. | 71/2.5 |
| 3,493,464 | 2/1970 | Bowers et al. | 162/161 |
| 3,728,213 | 4/1973 | Hinz | 162/161 |
| 3,864,468 | 2/1975 | Hyman et al. | 424/16 |
| 3,959,556 | 5/1976 | Morrison | 428/364 |
| 3,998,944 | 12/1976 | Long | 424/29 |
| 4,008,351 | 2/1977 | Inoue et al. | 424/412 |
| 4,111,922 | 9/1978 | Beede et al. | 526/292 |
| 4,124,135 | 11/1978 | Weder et al. | 220/4 B |
| 4,333,267 | 6/1982 | Witte | 47/72 |
| 4,343,853 | 10/1982 | Morrison | 428/33 |
| 4,401,700 | 8/1983 | Weder et al. | 428/17 |
| 4,401,712 | 8/1983 | Morrison | 428/289 |
| 4,408,996 | 10/1983 | Baldwin | 8/490 |
| 4,663,077 | 5/1987 | Rei et al. | 252/364 |
| 4,666,706 | 5/1987 | Farquharson | 424/408 |
| 4,743,448 | 5/1988 | Bahadir et al. | 424/411 |
| 4,888,175 | 12/1989 | Burton, Jr. et al. | 424/411 |
| 4,989,396 | 2/1991 | Weder et al. | 53/397 |
| 5,007,229 | 4/1991 | Weder et al. | 53/397 |

OTHER PUBLICATIONS

Advertisement, Increase the life of cut flowers with XTEND floral container liner, produced by Xtend Plastic, a division of Xebec Platics, Inc. (date unknown).

*Primary Examiner*—Thurman K. Page
*Assistant Examiner*—Amy Hulina
*Attorney, Agent, or Firm*—Dunlap, Codding & Lee

[57] ABSTRACT

Treating an article with an agent capable of inhibiting the growth of bacteria and/or fungus in an item susceptible to decay due to growth of bacteria and/or fungus. The article either at least partially is wrapped about or receives therein at least a portion of the item. Some examples of articles are floral wrappings, artificial Easter Eggs, and Easter grass.

7 Claims, 3 Drawing Sheets

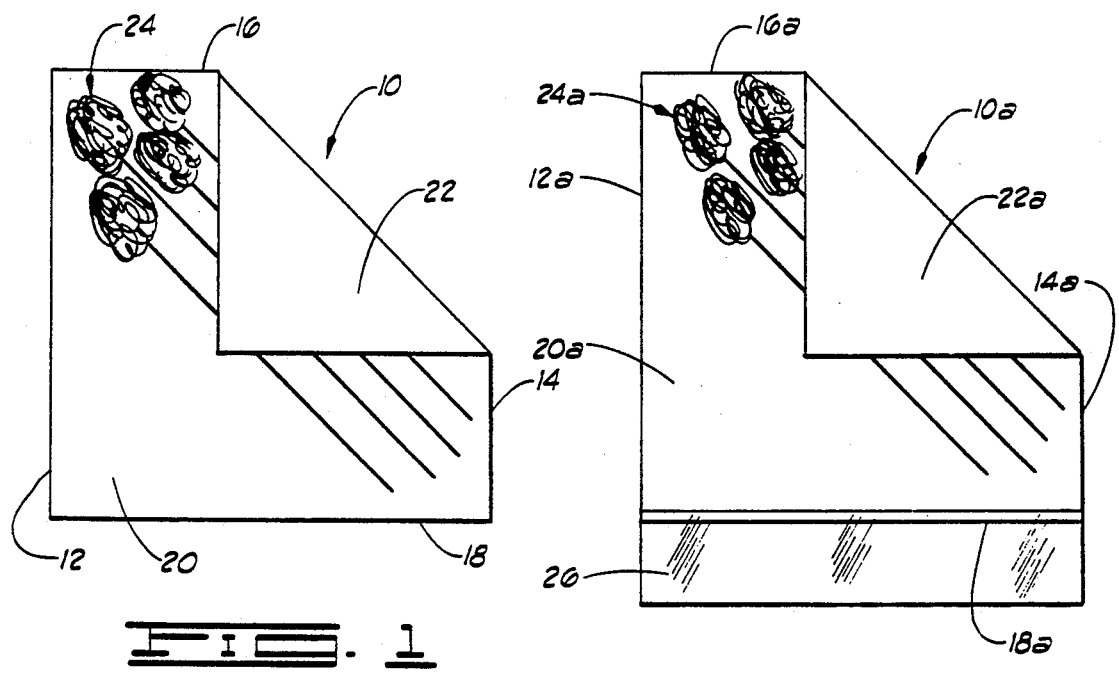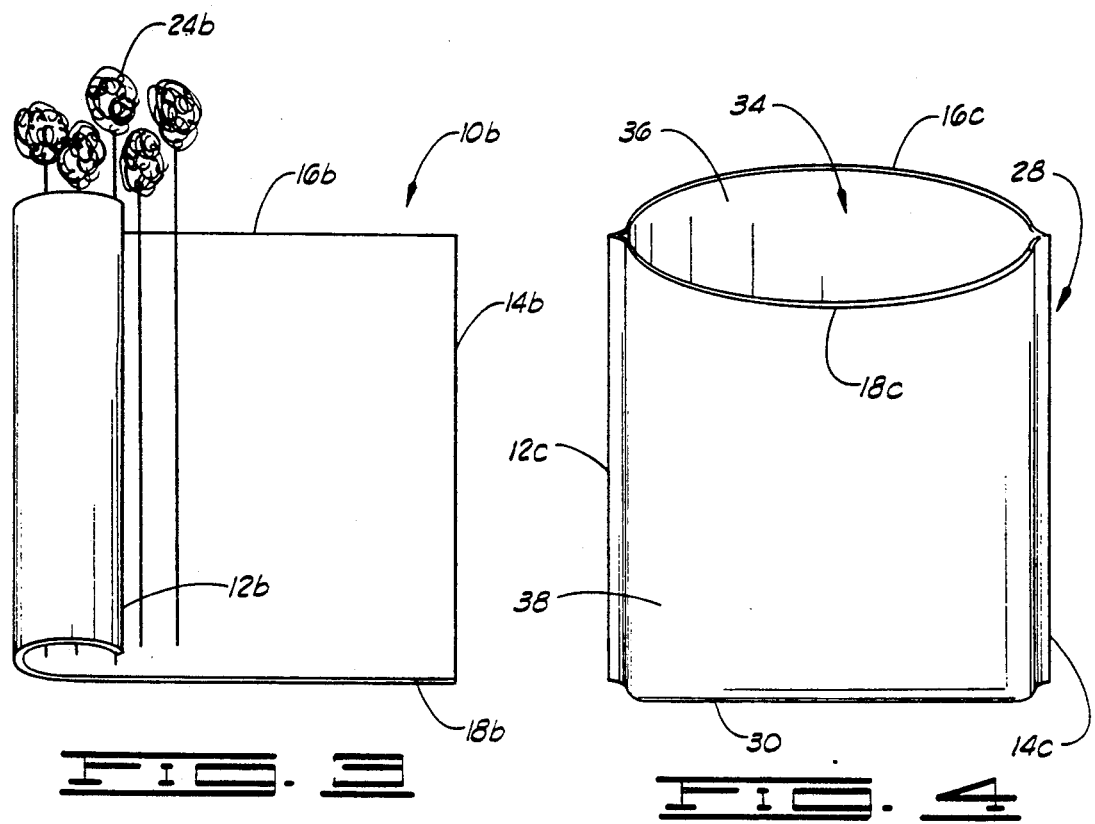

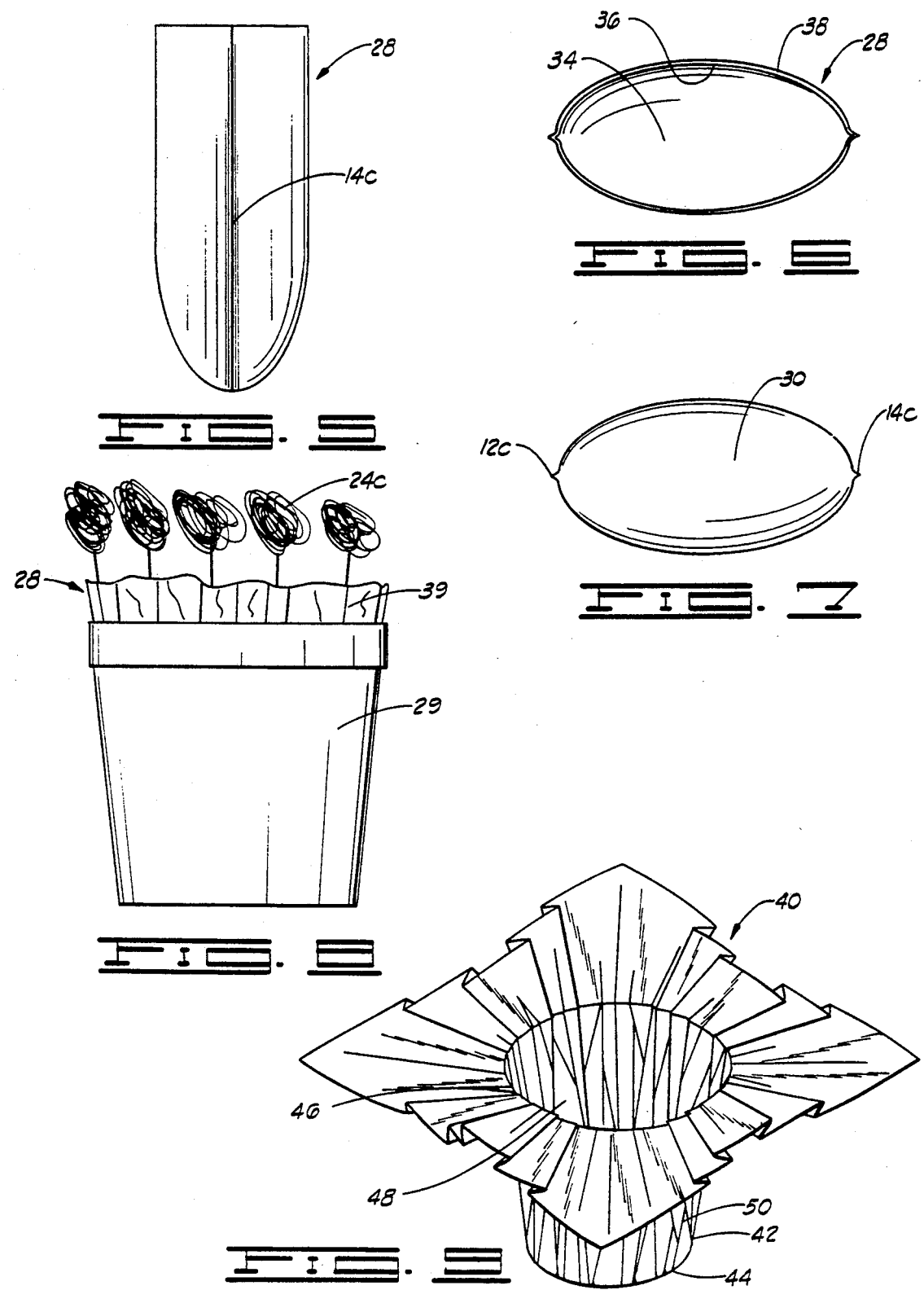

ANTIMICROBIAL MATERIAL AND METHODS

This application is a division of pending patent application U.S. Ser. No. 538,293, now abandoned filed Jun. 14, 1990, entitled, "ANTIMICROBIAL MATERIAL AND METHODS."

FIELD OF THE INVENTION

The present invention generally relates to articles that have been treated with agents capable of inhibiting the growth of bacteria and/or fungus and methods to prevent deterioration due to decay caused by bacteria and/or fungus of items contained in the treated articles. Some of the treated articles are wrappings for floral groupings, Easter grass and artificial Easter Eggs.

SUMMARY OF THE INVENTION

The present invention comprises an article treated with an agent capable of inhibiting the growth of bacteria and/or fungus in an item when the item is at least partially wrapped by or at least a portion item contained in the article. Preferably, the article is a sheet of material wrappable about a non-artificial floral grouping, a sheet of material forming a linear for a floral grouping container, a sheet of material forming a container for a floral grouping, an artificial (synthetic) Easter Egg or Easter grass. The item can be any item susceptible to decay from the growth of bacteria and/or fungus, such as non-artificial floral groupings or food. The present invention also comprises methods for inhibiting the growth of bacteria and/or fungus in items by wrapping about the items or receiving the items in an article treated with the agent previously described.

BRIEF DESCRIPTION OF THE DRAWINGS

FIG. 1 shows a perspective view of a treated sheet of material constructed in accordance with the present invention which is wrapped about a portion of a non-artificial floral grouping.

FIG. 2 shows a perspective view of a treated sheet of material constructed in accordance with the present invention having a self-adhesive portion attached thereto which is wrapped about at least a portion of a non-artificial floral grouping.

FIG. 3 shows a perspective view of a treated sheet of material constructed in accordance with the present invention having a preset curl in accordance with the present invention which rolls over at least a portion of a non-artificial floral grouping.

FIG. 4 shows a partial perspective view of a liner constructed in accordance with the present invention.

FIG. 5 shows a side view of the liner shown in FIG. 4.

FIG. 6 shows a top view of the liner shown in FIG. 4.

FIG. 7 shows a bottom view of the liner shown in FIG. 4.

FIG. 8 shows the liner of FIG. 4 disposed in a container and receiving a floral grouping.

FIG. 9 shows a partial perspective view of a flower pot of the present invention.

DETAILED DESCRIPTION OF PREFERRED EMBODIMENTS

Figures 10, 11:
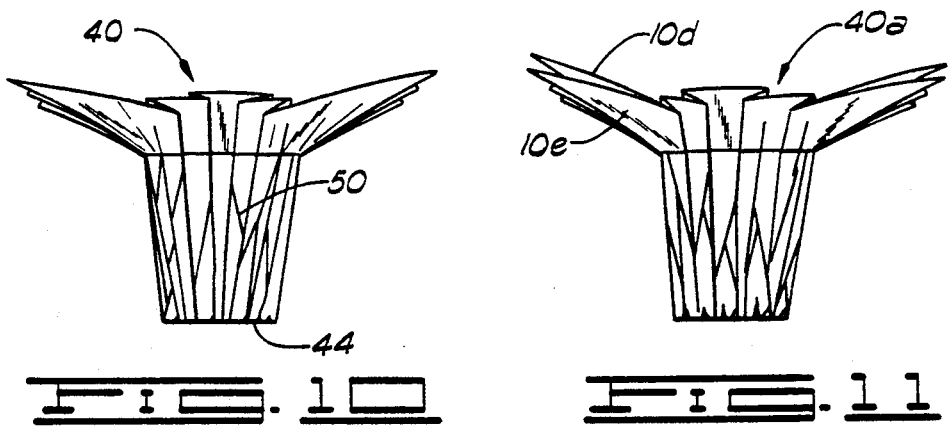
FIG. 10 shows a side view of the flower pot of FIG. 9.
FIG. 11 shows a side view of a flower pot of the present invention made from two sheets of material.

The attractiveness and utility of certain items, such as non-artificial floral groupings, diminish due to the deterioration caused by the growth of bacteria and/or fungus in the item. If the growth of the bacteria and/or fungus can be reduced in the item, the item can be useful for a longer period of time which decreases the cost of replacement. The present invention effectively delays the onset of deterioration of items susceptible to decay by inhibiting the growth of bacteria and/or fungus therein.

In accordance with the present invention, items susceptible to decay from bacteria and/or fungus are at least partially covered by or contained within an article treated with an agent capable of inhibiting the growth of either bacteria or fungus or both. Preferably, the agent is an antimicrobial agent which means that the agent possesses antifungal and antibacterial (bacteriostatic or bacteriocidal) properties, but the term "agent" as used herein may mean an agent possessing either antifungal, antibacterial or antimicrobial properties.

Preferably, the item to be protected from decay is a non-artificial floral grouping. A "non-artificial floral grouping" means cut fresh flowers, other fresh plants whether or not potted in soil, or other floral materials and may include other secondary plants and/or ornamentation which add to the aesthetics of the overall floral grouping. A "non-artificial floral grouping" can also be a single bud, flower or plant.

In accordance with the present invention, a sheet of material 10 treated with an agent capable of inhibiting the growth of bacteria and/or fungus in a non-artificial floral grouping is wrapped about at least a portion of the non-artificial floral grouping. The sheet of material 10 comprises a first end 12, a second end 14, a third end 16 and a fourth end 18. Additionally, the sheet of material 10 comprises an interior surface 20 and an exterior surface 22.

The sheet of material 10 may be of any size or shape that suitably wraps about the desired portion of the non-artificial floral grouping 24, and may be constructed from a variety of materials which are wrappable about a non-artificial floral grouping 24. Some examples of suitable materials are man-made organic film, paper or other cellulose-containing material, natural or synthetic fabrics, foil, or any combination of the foregoing.

In one preferred embodiment, the material 10 is constructed from a relatively thin film of a substantially non-shape sustaining man-made organic polymer film. The term "man-made organic polymer film" means a man-made resin such as a polypropylene as opposed to naturally occurring resins such as cellophane.

A man-made organic polymer film is relatively strong and not as subject to tearing (substantially non-tearable), as might be the case with paper or foil. The man-made organic polymer film is a substantially linearly linked processed organic polymer film and is a synthetic linear chain organic polymer where the carbon atoms are substantially linearly linked. Such films are synthetic polymers formed or synthesized from monomers. Further, a relatively substantially linearly linked processed organic polymer film is virtually waterproof which may be desirable in many applications such as wrapping a floral grouping.

Additionally, a relatively thin film of substantially linearly linked processed organic polymer does not substantially deteriorate in sunlight. Processed organic polymer films having carbon atoms both linearly linked and cross linked, and some cross linked polymer films, also may be suitable for use in the present invention provided such films are substantially flexible and can be made in a sheet-like format for wrapping purposes consistent with the present invention.

FIGS. 1-3 show preferred embodiments of the sheet of material of the present invention. Referring to FIG. 1, a non-artificial floral grouping 24 is disposed on the interior surface 20 of the sheet of material 10, and the sheet of material 10 is wrapped about at least a portion of the non-artificial floral grouping 24. FIG. 1 only shows part of the second end 14 wrapped about the floral grouping. Preferably, a portion of the first end 12 is also wrapped about the floral grouping 24.

In FIG. 2, the sheet of material 10a further comprises a self adhering material 26 secured to the fourth end 18a of the sheet of material 10a. The cling material 26 permits the securing of the sheet of material 26 about the non-artificial floral grouping 24a since the cling material sticks or clings to itself and to the sheet of material 10a. A complete disclosure of the cling material (or self adhering material) in U.S. Ser. No. 07/368,597 filed Jun. 20, 1989, now U.S. Pat. No. 5,007,229 entitled Self Adhering Wrapping Material is hereby incorporated by reference into the present application.

In FIG. 3, the sheet of material 10b has a curl preset in the material such that the first end 12b of the material 10b in an unrestrained condition rolls over itself forming a roll of the material wherein the non-artificial floral grouping 24b is disposable in the roll of the material. A complete disclosure of the curl wrap in U.S. Ser. No. 07/393,992 filed Aug. 15, 1989, now now U.S. Pat. No. 4,989,396 entitled Curl Wrap and Methods for Using Same is hereby incorporated by reference into the present application.

In accordance with the present invention, the sheet of material may be folded, glued, sealed or joined together by any method to form receptacles receiving non-artificial floral groupings 24. Referring to FIG. 4, a sheet of material has been folded in half so that the third end 16c and the fourth end 18c may contact, and the first end 12c and the second end 14c are respectively secured together to form a bag-like receptacle called a liner 28. The liner 28 is preferably non-shape sustaining, and therefore conforms to the shape of the container. Preferably, the liner 28 is constructed from a man-made organic polymer film.

The liner 28 is sized to receive a non-artificial floral grouping 24c. The liner 28 comprises an a closed lower end 30, an open upper end having an object opening 34 extending therethrough sufficiently sized to receive at least a portion of the non-artificial floral grouping 24c. Additionally, the liner 28 has an interior surface 36 adjacent the object opening 34 and an exterior surface 38.

The liner 28 may comprise more than one sheet of material which may be treated with an agent described herein or remain untreated. If the liner 28 comprises more than one sheet of material, the sheet of material 10 which has been treated with the agent comprises the interior surface 36 of the liner 28.

Preferably, the liner 28 is placed in any type of container 29 capable of receiving at least a portion of the non-artificial floral grouping 24. The liner 28 is preferably a little larger than the container 29, although any size or shape of the liner 28 may be used that allows the liner to function as described herein. Most preferably, the liner 28 is decoratively colored, embossed and/or printed with a design in order to aesthically enhance the appearance of the container 29. The liner 28 may also form a border 39 extending from the container 29 to enhance the appearance thereof, and make the effects of the agent available to the portion of the non-artificial floral grouping 24 extending beyond the container 29.

Preferably, the liner 28 is treated with the agent as described hereafter after the liner 28 has been formed. The non-artificial floral grouping 24 is disposed in the liner positioned in the container 29 as shown in FIG. 8. The linear 28 is in close proximity to or contacts the non-artificial floral groupings 24 which inhibits the growth of bacteria and/or fungus.

The treated sheet of material 10 may also be formed into a container capable of receiving at least a portion of a non-artificial floral grouping 24. One such container of the present invention comprises a flower pot, generally designated by the numeral 40, shown in FIG. 9. A full disclosure of a preferred flower pot 40 and its variations are found in U.S. Pat. No. 4,773,182 issued Sep. 27, 1988, entitled Article Forming System which is hereby incorporated by reference.

The flower pot 40 is preferably formed from at least one sheet of material which has been treated by an agent as described herein, and may be formed by a plurality of sheets of material so long as at least a portion of one sheet of material has been treated in accordance with the present invention. Referring to FIGS. 9-10, the flower pot 40 is formed into a base 42 having a closed lower end 44, and an open upper end 46 with an object opening 48 extending therethrough. The base 42 is preferably formed by permanently fixing a portion of the sheet of material into a plurality of overlapping folds 50 to form the base 42 and for cooperating to retain the base 42 in the formed shape. Referring to FIG. 11, the flower pot 40a is formed from a treated sheet of material 10d and untreated sheet of material 10e.

Preferably, the sheet of material 10 is constructed from a relatively thin man-made organic polymer film which normally is flexible and substantially non-shape sustaining. The flower pot 40 formed from this sheet of material is flexible and may be substantially flattened and then unflattened to assume the original shape of the formed container without substantial loss of the preformed shape thereby providing the flexible yet shape-sustaining nature of the formed container.

More preferably, the sheet of material forming the container has a thickness of less than about 1.5 mil and the container has a decorative border 52 extending outwardly from the open upper end 46 of the base 42.

In accordance with the present invention, other articles may be treated which contact items susceptible to decay from the growth of bacteria and/or fungus. Some of these articles are artificial Easter Eggs and Easter grass.

Figure 12:
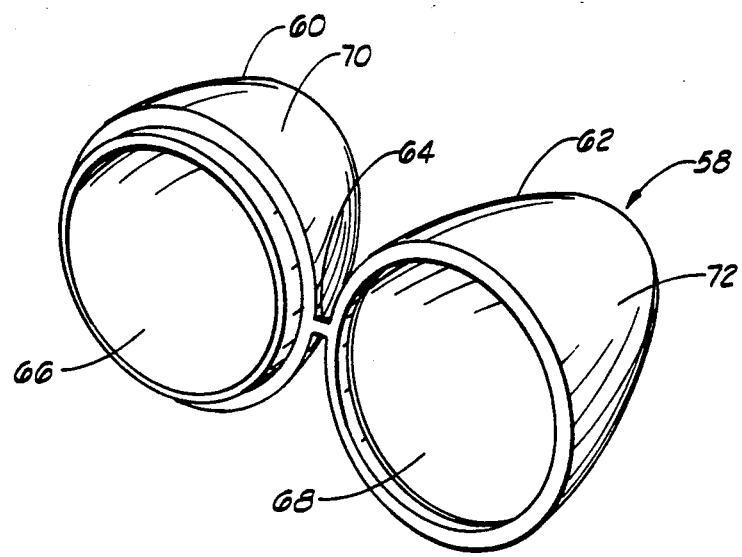
FIG. 12 shows an Easter Egg of the present invention.

Artificial Easter Eggs are hollow containers into which items such as candy may be disposed. An example of one such Easter Egg is disclosed in U.S. Pat. No. 4,124,135 issued Nov. 7, 1978, entitled Hinged Plastic Easter Egg which is hereby incorporated by reference into the present application, and is shown in FIG. 12.

Preferably the Easter Egg 58 is constructed from plastic, although other suitable materials may be used with permit the Easter Egg 58 to function as described herein.

Preferably, the Easter Egg 58 comprises a hollow Easter egg 58 constructed of two halves 60 and 62. The two halves 60 and 62 releasably join together, preferably by hinge 64. The Easter Egg 58 further comprises an interior wall 66 and 68, and exterior wall 70 and 72 respectively of halves 60 and 62 which are substantially continuous when halves 60 and 62 are connected.

The agent may be incorporated into the Easter Egg 58 prior to formation of same, or at least a portion of formed Easter Egg 58 may be treated with the agent by any method described herein. Preferably, at least a portion of the interior walls 66 and 68 are treated with the agent.

Figure 13:
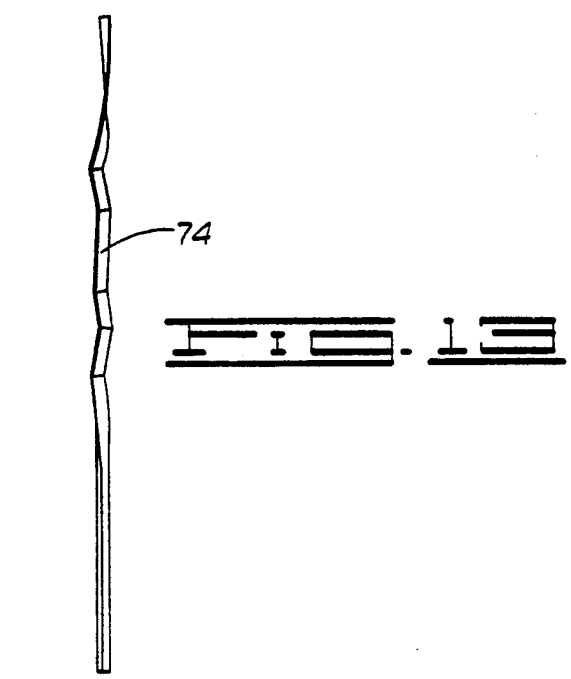
FIG. 13 shows a strand of Easter grass of the present invention.

An Easter grass 74 treated with an agent of the present invention is shown in FIG. 13. Examples of untreated Easter grass 74 are disclosed in U.S. Pat. No. 4,292,266 issued Sep. 29, 1981, entitled Process for making Decorative Grass and U.S. Pat. No. 4,401,700 issued Aug. 30, 1983, entitled Composition for Decorative Grass, which are hereby incorporated by reference into the present application.

Another application for the present application is to treat lids (not shown) for containers having foods items for animals and humans. The lids not only provide a physical barrier to bacteria and/or fungus, but also provide continued protection of the food item due to their ability to inhibit the growth of bacteria and/or fungus. Preferable agents are Oxy Tetracycline (such as Teramicine by Phizer) and Citemetrina (Piretroid by Russell Uclaff).

The agent used to treat the article (sheet of material 10, Easter Egg 58, Easter grass 74 or lids) will vary with the construction material used, the effect desired, and whether the agent has been incorporated prior to formation of the article or applied after the article has been formed. If the article is treated before formation of the article, the formation process may involve high temperatures which could effect the selection of the agent used.

Agents known to be compatible with a variety of polymers are the halogenated aromatic nitriles such as tetrachloroisophthalonitrile; Fungaflor, which is a salt of imazilil sulfate, made by Janssen Pharmaceuticals; 3,5,3,4'-tetrachlorosalicylanilide also known as Irgasan, made by Ciba-Geigy Company; and dichlorophene (2,2'-methylenebis-4-chlorophenol made by Givaudan Corporation).

The amount of the agents used is dependent upon the results sought and the use of the article. Generally, amounts of the agents ranging from 0.1% to about 0.5% by weight of the finished product may be used.

"Treating" the article means applying to or incorporating in the article an agent capable of inhibiting the growth of bacteria and/or fungus in an item which is contacted by the article. The agents may be applied by any method including, spraying, brushing, immersing the article in the agent or exposure of the article to agent-containing gas. Additionally, the agent may be incorporated into a dye, lacquer, tape, label or other medium applied to the article. The entire article may be treated, or only a portion thereof. Preferably, if only a portion of the article is treated, it is that portion in closest proximity to the item to be protected against bacterial and/or fungal growth. The agent may also be incorporated into the article prior to formation of the article.

Generally, the bacteria and/or fungus will be inhibited in the item due to the contact of the treated article with the item during the period of contact until the agent is substantially dissipated from the article. The duration of action of the agent will depend, in part, upon the agent used, the concentration of the agent, and the exposure of the agent to atmospheric conditions.

Changes may be made in the construction and operation of the various components and assemblies described herein and changes may be made in the steps or sequence of steps of the methods described herein without departing from the spirit and the scope of the invention as defined in the following claims.

What is claimed is:

1. A sheet of material wrappable about a non-artificial floral grouping, comprising:

a non-artificial floral grouping comprising cut flowers and/or plants;

a sheet of material having an upper surface, a lower surface, a first end, and a second end, the sheet of material sized to wrap about and substantially surround and encompass the non-artificial floral grouping, the sheet of material treated with an agent selected from the group consisting of (a) tetrachloroisophthalonitrile, (b) a selected salt of imazilil sulfate (Fungaflor), (c) 3,5,3,4'-tetrachlorosalicylanilide, (d) 2,2'-methylenebis-4-chlorophenol, or (e) combinations thereof, the agent capable of inhibiting the growth of bacteria and/or fungus on a non-artificial floral grouping susceptible to decay due to the growth of bacteria and/or fungus thereon while the floral grouping is in contact with the sheet of material, wherein the agent is capable of being applied to a surface of the sheet of material, and wherein the agent is capable of being incorporated into the sheet of material; and wherein the sheet of material is selected from the group consisting of (a) a sheet of material having a present curl in the sheet of material, (c) a sheet of material having a cling material secured to a portion of thereof, or (d) any combination thereof.

2. The sheet of material of claim 1 wherein the cling material is capable of connecting to the sheet of material and itself upon contacting engagement in order to secure the sheet of material about at least a portion of the non-artificial floral grouping.

3. The sheet of material of claim 1 wherein the curl is preset in the sheet of material such that both the first end and the second end of the sheet of material in an unrestrained condition rolls over itself forming a roll of the material, the roll being capable of being unrolled and then re-rolled, wherein the floral grouping is disposable in the roll of the sheet of material.

4. The sheet of material of claim 1 wherein the agent is applied to the sheet of material by the group consisting of spraying the agent thereupon, painting the agent thereupon, brushing the agent thereupon, immersing the sheet of material in the agent, exposing the sheet of material to agent-containing gas, or any combination thereof.

5. The sheet of material of claim 1 wherein the agent may be incorporated into a lacquer before the agent is disposed upon the sheet of material.

6. The sheet of material of claim 5 wherein the lacquer also includes a dye.

7. The sheet of material of claim 1 wherein the agent may also be incorporated into the group consisting of a tape, a label, or any combination thereof, after at least one of the foregoing is disposed upon the sheet of material.

* * * * *